(12) United States Patent
Dye

(10) Patent No.: US 10,226,558 B2
(45) Date of Patent: Mar. 12, 2019

(54) CANNULA APPARATUS AND VENTRICULAR ASSIST SYSTEMS USING THE CANNULA APPARATUS

(75) Inventor: Kenneth R. Dye, Neptune Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1272 days.

(21) Appl. No.: 14/117,464

(22) PCT Filed: May 10, 2012

(86) PCT No.: PCT/US2012/037202
§ 371 (c)(1),
(2), (4) Date: Dec. 31, 2014

(87) PCT Pub. No.: WO2012/158437
PCT Pub. Date: Nov. 22, 2012

(65) Prior Publication Data
US 2015/0104331 A1    Apr. 16, 2015

Related U.S. Application Data

(60) Provisional application No. 61/485,752, filed on May 13, 2011.

(51) Int. Cl.
*A61M 1/12* (2006.01)
*A61M 1/10* (2006.01)

(52) U.S. Cl.
CPC .......... *A61M 1/1008* (2014.02); *A61M 1/101* (2013.01); *A61M 1/122* (2014.02); *A61M 1/12* (2013.01); *A61M 2209/04* (2013.01)

(58) Field of Classification Search
CPC ... A61M 1/122; A61M 1/1006; A61M 1/1008
See application file for complete search history.

(56) References Cited

U.S. PATENT DOCUMENTS

| | | | |
|---|---|---|---|
| 3,995,517 A * | 12/1976 | Smith | B26D 7/30 177/121 |
| 3,995,617 A | 12/1976 | Watkins et al. | |
| 6,132,364 A | 10/2000 | Rottenberg et al. | |
| 6,254,578 B1 | 7/2001 | Grooters et al. | |
| 6,398,714 B1 | 6/2002 | Verkerke et al. | |
| 6,726,648 B2 | 4/2004 | Kaplon et al. | |

(Continued)

FOREIGN PATENT DOCUMENTS

| | | |
|---|---|---|
| WO | WO 98/28034 A1 | 7/1998 |
| WO | WO 00/37139 A1 | 6/2000 |

(Continued)

OTHER PUBLICATIONS

Supplementary Search Report dated Jul. 30, 2015, for International Application No. PCT/US2012/037202. 2 pages.

(Continued)

*Primary Examiner* — Bruce E Snow
(74) *Attorney, Agent, or Firm* — Mueting, Raasch & Gebhardt, P.A.

(57) ABSTRACT

Cannula apparatus, ventricular assist systems including the cannula apparatus, and methods of priming and placing the cannula apparatus and ventricular assist systems are described herein.

13 Claims, 6 Drawing Sheets

(56) References Cited

U.S. PATENT DOCUMENTS

| | | | |
|---|---|---|---|
| 6,790,171 B1 | 9/2004 | Gründeman et al. | |
| 6,974,436 B1 | 12/2005 | Aboul-Hosn et al. | |
| 6,979,318 B1 | 12/2005 | McDonald et al. | |
| 8,029,491 B2* | 10/2011 | Aboul-Hosn | A61M 1/367 604/28 |
| 2003/0023255 A1 | 1/2003 | Miles et al. | |
| 2004/0236170 A1 | 11/2004 | Kim | |
| 2007/0156006 A1 | 7/2007 | Smith et al. | |
| 2009/0203957 A1 | 8/2009 | LaRose et al. | |
| 2015/0231317 A1* | 8/2015 | Schima | A61M 1/122 600/16 |

FOREIGN PATENT DOCUMENTS

| | | | |
|---|---|---|---|
| WO | WO 2012/158437 A2 | 11/2012 | |
| WO | WO 2012/158437 A3 | 11/2012 | |

OTHER PUBLICATIONS

International Preliminary Report on Patentability dated Nov. 19, 2013, for International Application No. PCT/US2012/037202.

* cited by examiner

CANNULA APPARATUS AND VENTRICULAR ASSIST SYSTEMS USING THE CANNULA APPARATUS

RELATED APPLICATION

The present application is a U.S. National Stage Application of International Application No. PCT/US2012/0037202, titled CANNULA APPARATUS AND VENTRICULAR ASSIST SYSTEM USING THE CANNULA APPARATUS, filed on May 10, 2012, which claims the benefit under 35 U.S.C. § 119(e) of U.S. Provisional Patent Application No. 61/485,752, filed on May 13, 2011 and titled CANNULA APPARATUS AND VENTRICULAR ASSIST SYSTEMS USING THE CANNULA APPARATUS, each of which is hereby incorporated by reference in its entirety.

Cannula apparatus, ventricular assist systems including the cannula apparatus, and methods of priming and placing the cannula apparatus and ventricular assist systems are described herein.

A growing number of open-heart surgical programs now augment cardiac function in failing hearts with Ventricular Assist Devices (VAD). These devices can offer a bridge to cardiac transplantation, ventricular recovery, or long-term post-implant destination therapy (home recovery). A number of various Ventricular Assist devices now have regulatory approval, are commercially available, and are clinically implanted each year. Despite the benefits these devices offer, their insertion is fraught with technical challenges and potential complications that can occur during the time of device implantation, and possibly extending well beyond the post-implant recovery period.

Among the potential issues associated with implantation of VAD's is that the inflow cannulas used in the devices typically require muscle coring. In other words, apical ventricular inflow cannulas are designed to be placed following direct ventricular coring (cutting of a muscle plug) to place the device. This is necessary as current inflow cannulas have a distal tip with one distal drainage hole that is at risk of suction occlusion, thereby requiring direct muscle coring to ensure that the distal cannula tip is free from adjacent trabeculated fibro muscular attachments or other intraventricular structures. Examples of devices and systems that use this approach may be found in U.S. Pat. No. 6,726,648 (Kaplon et al.) and in US 2004/0236170 (Kim).

One complication faced during implantation of a VAD is the possibility of stroke. One potential cause of a stroke is the presence of ventricular intracavity free air and air introduced into the VAD during pump priming or device insertion. This complication, although known, remains extremely problematic. Surgical maneuvers, such as the use of hypodermic needles placed directly into the woven material of the outflow graft, or a connection to a designated suction line may be used to assist in the evacuation of air from either the heart or device chamber. Methods of using needles to puncture outflow graft material, however, add another potential source for post implant bleeding that can aid in prolonging the procedure, or introduce the risk re-operative exploration following the initial device implantation, should delayed bleeding occur. The use of designated suction lines can also "pull" or agitate blood forward under vacuum, which can potentially result in the development of micro air bubbles within the outflow graft, which is sewn onto the ascending or descending aorta.

SUMMARY

Cannula apparatus and ventricular assist systems including the cannula apparatus are described herein. In addition, methods of priming and placing the cannula apparatus and ventricular assist systems are also described herein. The cannula apparatus described herein include an outer and inner cannula that can be moved between an open and closed arrangement in which openings in the inner and outer cannula are either open or closed.

The cannula apparatus described herein may preferably be configured to be directly inserted into the ventricular chamber without the need for coring of heart muscle, or to remove trabeculated fibro-muscle attachments, which can occlude of the distal drainage tip of a traditional ventricular inflow cannula. The cannula apparatus described herein also preferably include multiple openings through the sidewall of the cannula to potentially reduce the occurrence of blockages that would prevent sufficient blood flow into the cannula apparatus. Furthermore, in addition to maintaining the cannula apparatus in a primed state, closure of the openings of the cannula apparatus during trans-ventricular placement of the device preferably limits or prevents the entry of tissue into the cannula apparatus that could result in blockage and/or reduced flow or embolization of tissue fragments.

The cannula apparatus and the ventricular assist systems described herein may, in some embodiments, be primed and maintain full priming without off loading (draining) of the ventricle before placement of the cannula apparatus. That will likely reduce the introduction of intracavitary or device free-air and potentially avoid the inherent risks that exist when placing a patient onto a cardiopulmonary bypass circuit (for extracorporeal circulation) during placement of a VAD.

In one aspect, embodiments of the cannula apparatus described herein may include an outer cannula comprising a proximal end and a distal end, wherein the outer cannula further comprises: a sidewall defining an interior volume extending from the distal end of the outer cannula to the proximal end, and a plurality of first openings extending through the sidewall into the interior volume of the outer cannula between the proximal end and the distal end of the outer cannula. The cannula apparatus may further include an inner cannula comprising a proximal end and distal end, wherein at least a portion of the inner cannula is located within the interior volume of the outer cannula, and wherein the inner cannula further comprises: a sidewall defining an interior volume extending from the distal end of the inner cannula to the proximal end, and a plurality of second openings extending through the sidewall into the interior volume of the inner cannula between the proximal end and the distal end of the inner cannula. The inner cannula and the outer cannula may have an open arrangement in which the first openings and the second openings are aligned such that fluid from outside of the outer cannula can flow into the interior volume of the inner cannula through the first and second openings. The inner cannula and the outer cannula may also have a closed arrangement in which the first openings and the second openings are offset such that the sidewall of the outer cannula blocks the plurality of second openings in the inner cannula and the sidewall of the inner cannula blocks the plurality of first openings in the outer cannula, wherein fluid from outside of the outer cannula does not flow into the interior volume of the inner cannula through the first and second openings. The proximal end of the cannula apparatus comprises a port, wherein fluid flowing into the interior volume of the inner cannula through the second openings passes out of the cannula apparatus through the port.

In another aspect, embodiments of the ventricular assist system described herein may include a blood pump; an outflow cannula in fluid communication with an outlet of the blood pump; and an inflow cannula apparatus comprising a port in fluid communication with an inlet of the blood pump. The inflow cannula apparatus may include an outer cannula comprising a proximal end and a distal end, a sidewall defining an interior volume extending from the distal end of the outer cannula to the proximal end, and a plurality of first openings extending through the sidewall into the interior volume of the outer cannula between the proximal end and the distal end of the outer cannula. The inflow cannula apparatus may also include an inner cannula comprising a proximal end and distal end, wherein at least a portion of the inner cannula is located within the interior volume of the outer cannula, and wherein the inner cannula further comprises: a sidewall defining an interior volume extending from the distal end of the inner cannula to the proximal end, and a plurality of second openings extending through the sidewall into the interior volume of the inner cannula between the proximal end and the distal end of the inner cannula. The inner cannula and the outer cannula may have an open arrangement in which the first openings and the second openings are aligned such that fluid from outside of the outer cannula can flow into the interior volume of the inner cannula through the first and second openings. The inner cannula and the outer cannula may also have a closed arrangement in which the first openings and the second openings are offset such that the sidewall of the outer cannula blocks the plurality of second openings in the inner cannula and the sidewall of the inner cannula blocks the plurality of first openings in the outer cannula, wherein fluid from outside of the outer cannula does not flow into the interior volume of the inner cannula through the first and second openings. Fluid flowing into the interior volume of the inner cannula through the second openings passes out of the cannula apparatus through the port.

In some embodiments of the cannula apparatus and the ventricular assist systems described herein, the inner cannula and the outer cannula are configured to move relative to each other to selectively place the inner cannula and the outer cannula in the open arrangement or the closed arrangement.

In some embodiments of the cannula apparatus and the ventricular assist systems described herein, the inner cannula and the outer cannula are configured to rotate relative to each other to selectively place the inner cannula and the outer cannula in the open arrangement or the closed arrangement.

In some embodiments of the cannula apparatus and the ventricular assist systems described herein, the inner cannula and the outer cannula are configured for translational movement relative to each other to selectively place the inner cannula and the outer cannula in the open arrangement or the closed arrangement.

In some embodiments of the cannula apparatus and the ventricular assist systems described herein, all of the first openings of the plurality of first openings in the outer cannula are aligned with the second openings of the inner cannula when the inner and outer cannulas are in the open arrangement.

In some embodiments of the cannula apparatus and the ventricular assist systems described herein, only some of the first openings of the plurality of first openings in the outer cannula are aligned with the second openings of the inner cannula when the inner and outer cannulas are in the open arrangement.

In some embodiments of the cannula apparatus and the ventricular assist systems described herein, all of the first openings of the plurality of first openings are located proximally from the distal end of the outer cannula such that the distal end of the outer cannula is a closed distal end.

In some embodiments of the cannula apparatus and the ventricular assist systems described herein, a distal end of the cannula apparatus comprises a tapered distal end that narrows when moving distally along the cannula apparatus.

In some embodiments of the cannula apparatus and the ventricular assist systems described herein, the cannula apparatus comprises a locking mechanism configured to lock the inner cannula and the outer cannula in the open arrangement and the closed arrangement, whereby movement of out of the open arrangement or the closed arrangement is prevented when the inner and outer cannula are locked. In some embodiments, the locking mechanism comprises a collet and nut. In some embodiments, the locking mechanism comprises a locking pin.

In some embodiments of the cannula apparatus and the ventricular assist systems described herein, the cannula apparatus further comprises an attachment ring extending radially outward from a longitudinal axis extending through the cannula apparatus from the distal end of the outer body through the port.

In some embodiments of the cannula apparatus and the ventricular assist systems described herein, the cannula apparatus further comprises a sealing element located between the inner cannula and the outer cannula at a location distal from the port of the cannula apparatus. In some embodiments, the sealing element is located proximal to all of the first openings and the second openings.

In some embodiments of the cannula apparatus and the ventricular assist systems described herein, the port of the cannula apparatus comprises a connector configured for fluid-tight connection to a fluid line extending away from the port.

In some embodiments of the cannula apparatus and the ventricular assist systems described herein, the cannula apparatus includes a guidewire lumen isolated from the interior volume of the inner cannula.

In another aspect, methods of priming a ventricular assist system are described herein, where the ventricular assist system comprises a blood pump and a cannula apparatus (as described herein) attached to an inlet of the blood pump. The methods of priming may include submerging the blood pump and the cannula apparatus in a selected liquid, wherein the cannula apparatus is in the open configuration before or after submerging the blood pump and the cannula apparatus; operating the blood pump to prime the ventricular assist system; and moving the cannula apparatus to the closed arrangement while the ventricular assist system is submerged. In some methods of priming, the selected liquid comprises blood-compatible liquid.

In some embodiments, the method of priming may include attaching an outflow cannula to an outlet of the blood pump. In some methods, the outflow cannula is attached to the blood pump while the blood pump is submerged in the selected liquid.

The above summary is not intended to describe each embodiment or every implementation of any apparatus, systems and methods described herein. Rather, a more complete understanding of any apparatus, systems and methods described herein will become apparent and appreciated by reference to the following Description of Illustrative Embodiments and claims in view of the accompanying figures of the drawing.

DESCRIPTION OF ILLUSTRATIVE EMBODIMENTS

Figure 1:
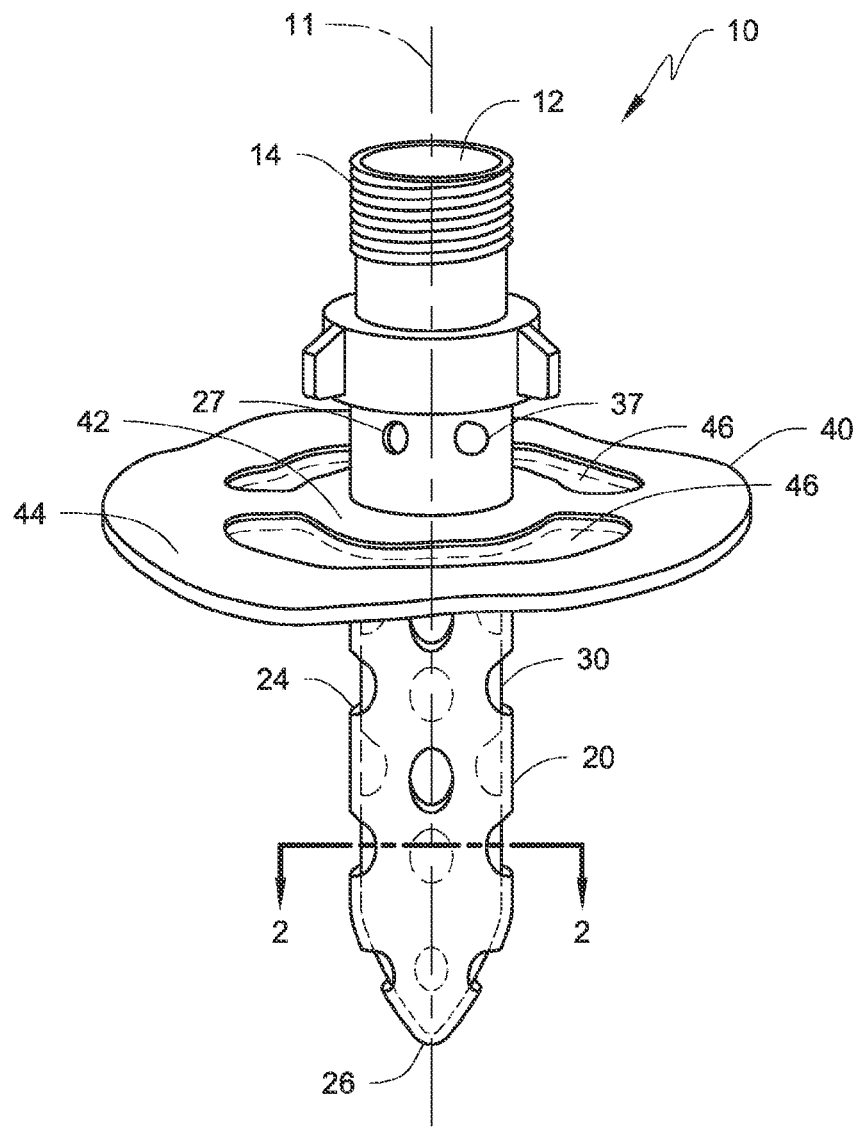
FIG. 1 is a perspective view of one illustrative embodiment of a cannula apparatus as described herein, with the cannula apparatus in a closed arrangement.

In the following description of illustrative embodiments described herein, reference is made to the accompanying figures of the drawing which form a part hereof, and in which are shown, by way of illustration, specific embodiments which may be practiced. It is to be understood that other embodiments may be utilized and structural changes may be made without departing from the scope of the present invention.

Figure 2:
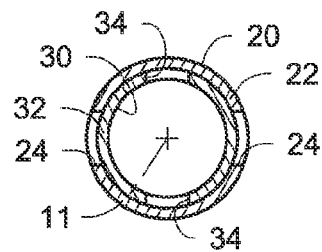
FIG. 2 is a cross-sectional view of the cannula apparatus of FIG. 1 taken along line 2-2 in FIG. 1.
Figure 3:
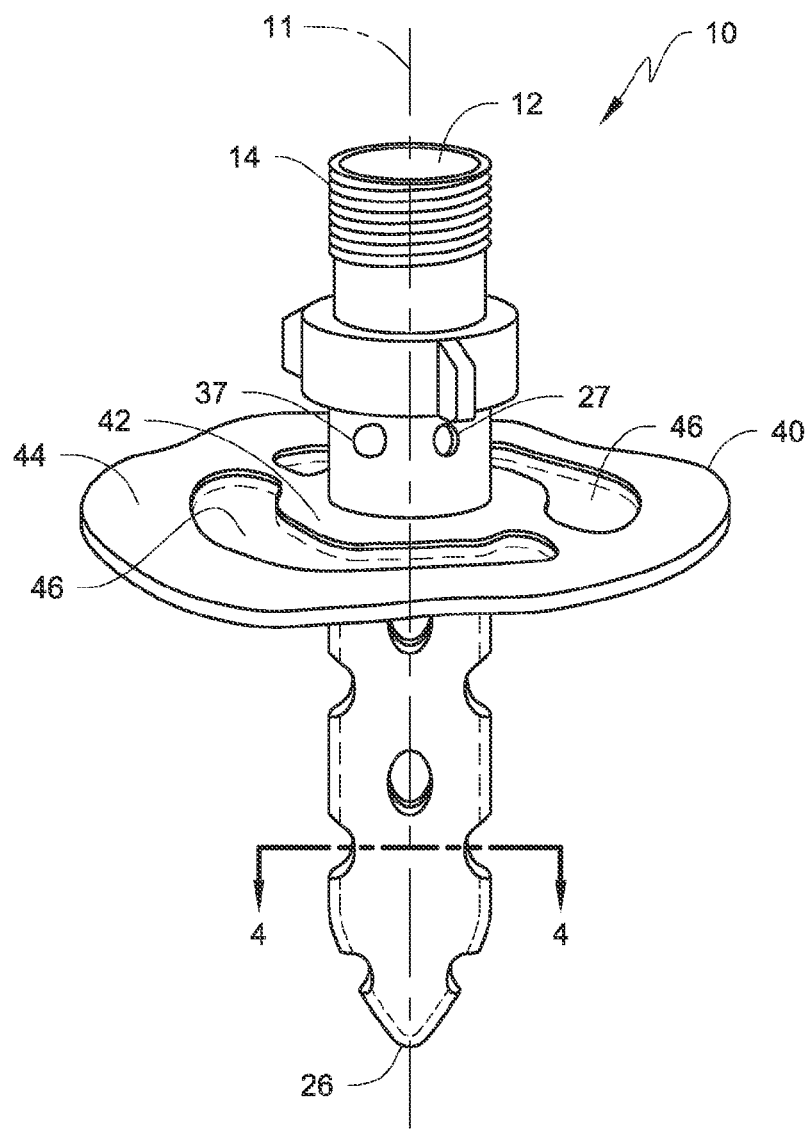
FIG. 3 is a perspective view of one illustrative embodiment of a cannula apparatus of FIG. 1, with the cannula apparatus in an open arrangement.
Figure 4:
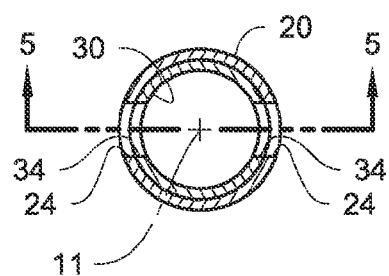
FIG. 4 is a cross-sectional view of the cannula apparatus of FIG. 3 taken along line 4-4 in FIG. 3.
Figure 5:
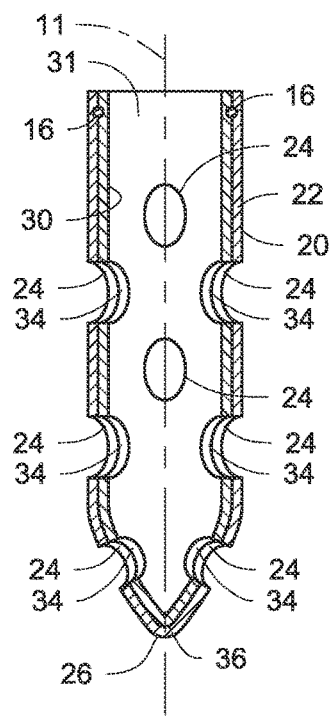
FIG. 5 is a cross-sectional view of the cannula apparatus of FIGS. 3 and 4 taken along line 5-5 in FIG. 4.

Referring to FIGS. 1-5, where one illustrative embodiment of a cannula apparatus for use with a ventricular assist system is depicted. In particular, FIG. 1 is a perspective view of the cannula apparatus 10, with the cannula apparatus 10 in a closed arrangement (as will be described in more detail herein). FIG. 2 is a cross-sectional view of the cannula apparatus 10 taken along line 2-2 in FIG. 1. FIG. 3 is a perspective view of the cannula apparatus 10, with the cannula apparatus 10 in an open arrangement. FIG. 4 is a cross-sectional view of the cannula apparatus 10 taken along line 4-4 in FIG. 3, and FIG. 5 is a cross-sectional view of the cannula apparatus 10 taken along line 5-5 in FIG. 4.

The cannula apparatus 10 includes an outer cannula 20, an inner cannula 30, and an attachment flange 40 extending outwardly from the inner and outer cannulas 20 and 30. A port 12 is provided at the proximal end of the cannula apparatus 10 such that fluid flowing into the interior volume 31 of the inner cannula 30 passes out of the cannula apparatus 10 through the port 12. Typically, the port 12 may preferably include connection structure to assist with fluid-tight connection of the cannula apparatus 10 to fluid line that may be connected to, e.g., a VAD. In the depicted embodiment, the connection structure is in the form of threads 14, although any other suitable connection structure such as, e.g., Luer Lock connectors, etc. may alternatively be used.

The outer cannula 20 has a proximal end located proximate the port 12 and a distal end 26 located distal from the port 12. A longitudinal axis 11 of the cannula apparatus 10 extends between the port 12 and the distal end 26 of the outer cannula 20. A sidewall 22 of the outer cannula 20 defines an interior volume extending from the distal end 26 of the outer cannula 20 to the proximal end of the outer cannula 20.

The outer cannula 20 includes a plurality of first openings 24 extending through the sidewall 22 into the interior volume of the outer cannula 20 between the proximal end of the outer cannula 20 and the distal end 26 of the outer cannula 20. The size, shape and arrangement of the openings 24 in the outer cannula 20 are illustrative only, i.e., outer cannulas used in other embodiments of cannula apparatus as described herein may be provided in other sizes, shapes, and/or arrangements.

The cannula apparatus 10 also includes an inner cannula 30 that also includes a proximal end closer to the port 12 and a distal end 36 located proximate the distal end 26 of the outer cannula 20. In some embodiments, inner cannula 30 may terminate short of the distal end 26 of the outer cannula 20 rather than extending to the distal end 26 of the inner cannula 20. As a result, at least a portion of the inner cannula 30 is located within the interior volume of the outer cannula 20.

In the depicted embodiment, the inner cannula 30 includes a sidewall 32 defining an interior volume 31 extending from the distal end 36 of the inner cannula 30 to the proximal end of the inner cannula 30. The inner cannula further includes a plurality of second openings 34 extending through the sidewall 32 into the interior volume 31 of the inner cannula 30 between the proximal end of the inner cannula 30 and the distal end 36 of the inner cannula 30.

In the depicted embodiment, the inner cannula 30 and the outer cannula 20 have an open arrangement (as depicted in FIGS. 1, 2, and 5) in which the first openings 24 in the outer cannula 20 and the second openings 34 in the inner cannula 30 are aligned such that fluid from outside of the outer cannula 20 can flow into the interior volume 31 of the inner cannula 30 through the first and second openings 24 and 34.

The inner cannula 30 and the outer cannula 20 of the cannula apparatus 10 also include a closed arrangement (as depicted in FIGS. 3 and 4) in which the first openings 24 and the second openings 34 are offset from each other such that the sidewall 22 of the outer cannula 20 blocks the plurality of second openings 34 in the inner cannula 30 and the sidewall 32 of the inner cannula 30 blocks the plurality of first openings 24 in the outer cannula 20, such that fluid from outside of the outer cannula 20 does not flow into the interior volume 31 of the inner cannula 30 through the first and second openings 24 and 34.

The cannula apparatus as described herein include, in the depicted embodiments, an inner cannula and an outer cannula that are configured to move relative to each other to selectively place the inner cannula and the outer cannula in the open arrangement or the closed arrangement. That relative movement may be accomplished by holding either one of the outer cannula or the inner cannula stationary while moving the other cannula or, in some embodiments, moving both cannulas relative to each other within the cannula apparatus.

In the illustrative embodiment depicted in FIGS. 1-5, one form of movement between the outer cannula 30 and the inner cannula 20 is depicted in the form of rotation about the longitudinal axis 11. In other words, the inner cannula 30 and the outer cannula 20 are configured to rotate relative to each other about the longitudinal axis 11 to selectively place the inner cannula 30 and the outer cannula 20 in the open arrangement (in which the openings 24 in the outer cannula 20 are aligned with the openings 34 in the inner cannula 30) or in the closed arrangement (in which the openings 24 in the outer cannula 20 are offset from the openings 34 in the inner cannula 30).

Figure 6:
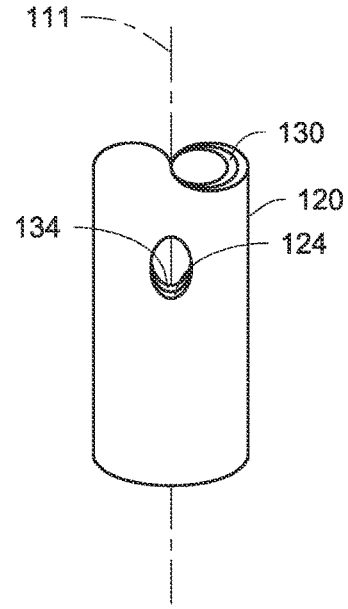
FIGS. 6 and 7 depict a portion of an alternative embodiment of a cannula apparatus as described herein, wherein translational movement is used to move the cannula apparatus from a closed arrangement to an open arrangement.
Figure 7:
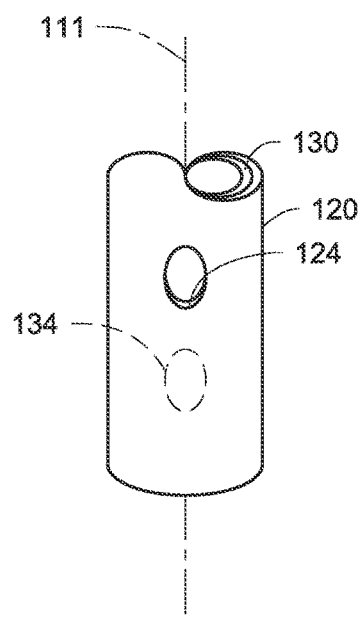

Referring to FIGS. 6 and 7, one alternative form of movement between an outer cannula 120 and the inner cannula 130 is depicted. In this alternative embodiment, the inner cannula 130 and the outer cannula 120 are configured for translational movement relative to each other along longitudinal axis 111 to selectively place the inner cannula 130 and the outer cannula 120 in the open arrangement (in which the openings 124 in the outer cannula 120 are aligned with the openings 134 in the inner cannula 130—see FIG. 6) or the closed arrangement (in which the openings 124 in the outer cannula 120 are offset from the openings 134 in the inner cannula 130—see FIG. 7).

In the cannula apparatus 10 depicted in FIGS. 1-5, all of the first openings 24 in the outer cannula 20 are aligned with the second openings 34 of the inner cannula 30 when the outer and inner cannulas 20 and 30 are in the open arrangement. In other embodiments, however, the all of the openings in the inner and outer cannulas may not necessarily be aligned with each other when the cannula apparatus is in the open arrangement (i.e., only some of the openings in the inner and outer cannulas may be aligned in some embodiments when the cannula apparatus is in the open arrangement). In still other embodiments, the openings in the inner and outer cannulas may be only partially aligned with each other when the cannula apparatus is in the open arrangement (in contrast to the depicted embodiment in which the openings 24 in the outer cannula 20 are completely aligned with the openings 34 in the inner cannula 30).

Figure 8:
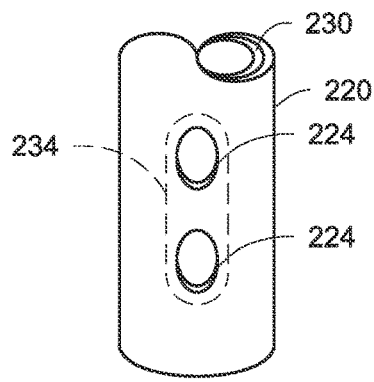
FIG. 8 depict a portion of another alternative embodiment of a cannula apparatus as described herein.

In yet other embodiments, the openings in the outer cannula may not be the same size and/or shape as the openings in the inner cannula (in contrast to the openings 24 in the outer cannula 20 which are the same size and/or shape as the openings 34 in the inner cannula 30). One potential example of this concept is depicted in FIG. 8 where an outer cannula 220 includes two (or more) openings 224 that can be aligned with one larger opening 234 in the inner cannula 230 when the cannula apparatus including the outer cannula 220 and the inner cannula 230 is in the open arrangement as depicted in FIG. 8.

In some embodiments of the cannula apparatus described herein, including the embodiment depicted in FIGS. 1-5, all of the openings 24 in the outer cannula 20 are located proximally from the distal end 26 of the outer cannula 20 such that the distal end 26 of the outer cannula 20 is a closed distal end. In other words, no tissue (and preferably also no fluid) can enter the outer cannula 20 or the inner cannula 30 through the distal end 26 of the outer cannula 20.

In some embodiments of the cannula apparatus described herein, including the embodiment depicted in FIGS. 1-5, the distal end of the cannula apparatus 10 may be in the form of a tapered distal end that narrows when moving distally along the longitudinal axis 11 extending through the cannula apparatus 10. Although the distal end 26 of the outer cannula 20 forms the distal end of the cannula apparatus 10 in the depicted embodiment, this arrangement may not always be found in all embodiments of the cannula apparatus described herein.

In some embodiments of the cannula apparatus described herein, including the embodiment depicted in FIGS. 1-5, the cannula apparatus may include a locking mechanism configured to lock the inner cannula and the outer cannula in the open arrangement and the closed arrangement. When locked in either arrangement, movement out of the open arrangement or the closed arrangement is prevented by the locking mechanism. In the illustrative embodiment depicted in FIGS. 1-5, the locking mechanism is in the form of a pair of openings 27 formed in the outer cannula 20 and a protrusion extending from the inner cannula 30. The protrusion 37 extends through or otherwise mechanically interlocks with one of the openings 27 to lock the outer cannula 20 and the inner cannula 30 in either the open arrangement or the closed arrangement. The protrusion 37 may be in the for in of a pin that is biased outwards by, e.g., a resilient element such as a spring, etc. The locking mechanism depicted in the embodiment of FIGS. 1-5 is illustrative only and many other structures could be substituted for it, e.g., a collet and locking nut, etc.

In some embodiments of the cannula apparatus described herein, including the embodiment depicted in FIGS. 1-5, the cannula apparatus may preferably include an attachment ring extending radially outward from the longitudinal axis extending through the cannula apparatus from the distal end of the outer body through the port of the inner cannula. In the illustrative embodiment of FIGS. 1-5, the attachment ring 40 is located between the port 12 and the openings 24 in the outer cannula such that, when the inner and outer cannulas 20 and 30 are located within a heart ventricle and the attachment ring is secured to the exterior surface of the heart, the openings 24 are all located within the ventricle (see, e.g., FIG. 10 described herein).

The attachment ring 40 of the cannula apparatus 10 may be configured as a sewing ring that would allow for sutures to be placed either before or following ventricular cannula insertion, and would preferably allow for eversion of myocardial muscle, by way of, e.g., separate rims of inner and outer suture receptive material (e.g., felt). In the depicted embodiment, the attachment ring 40 includes an inner ring 42 and an outer ring 44 of felt or other material amenable to suturing. The depicted attachment ring 40 may also include, e.g., a layer of liquid impervious material 46 that is exposed between the inner ring 42 and the outer ring 44 of felt material. A sewing ring constructed in this manner may potentially improve the purchasing and buttress support of the sewing ring 40 to the heart surface and may also potentially provide improved hemostasis at the cannula insertion site. Such a sewing ring 40 may also allow for placement of mattress sutures and a running layer of suture material around the outer perimeter of the ring 40 to assist in securing the sewing ring 40 and, thus, cannula apparatus 10 in place while lessening the risk of bleeding.

In some embodiments of the cannula apparatus described herein, including the embodiment depicted in FIGS. 1-5, the cannula apparatus may preferably include a sealing element 16 (see, e.g., FIG. 5) that is located between the inner cannula 30 and the outer cannula 20 at a location distal from the port 12 of the cannula apparatus 10. It may be preferred that the sealing element 16 be located proximal to all of the openings 24 in the outer cannula 20 as well as all of the openings 34 in the inner cannula 30 as, e.g., seen in FIG. 5.

Figure 9:
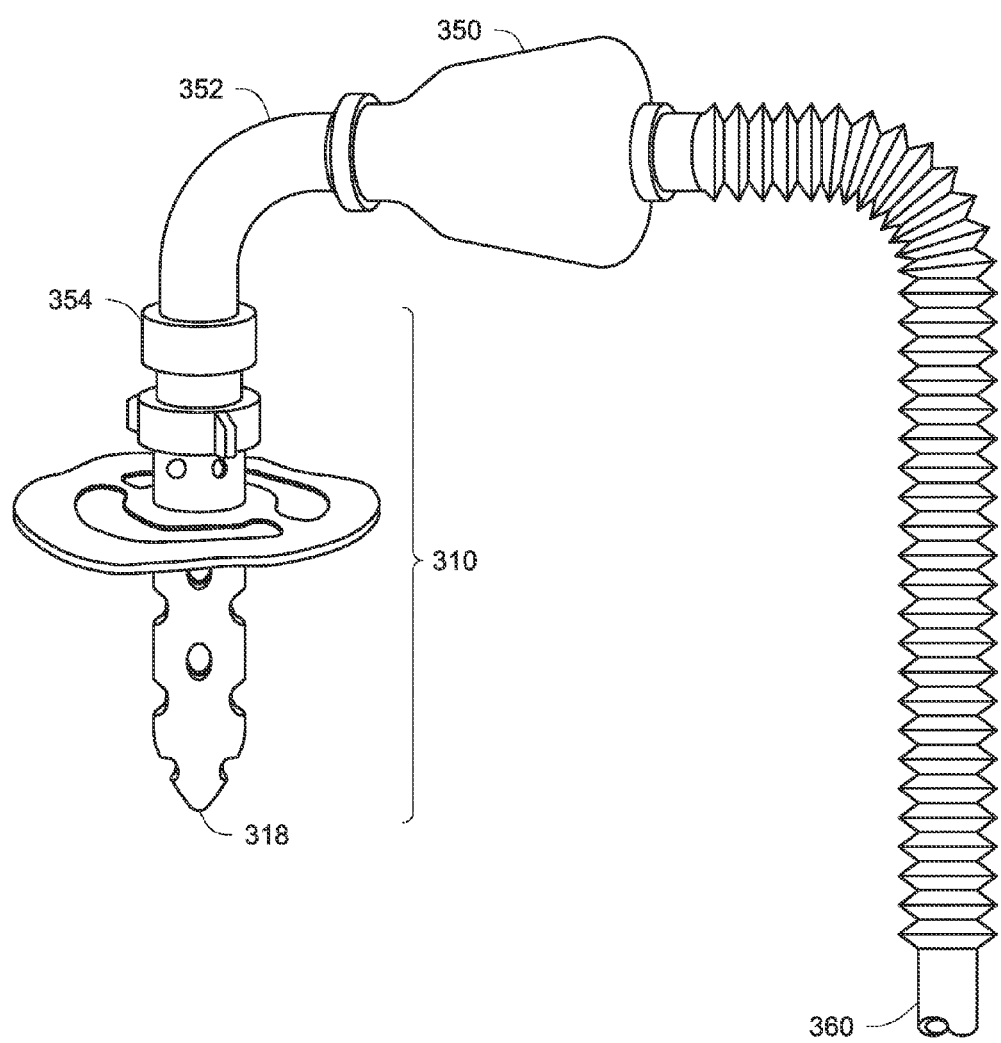
FIG. 9 is a perspective view of one illustrative embodiment of a ventricular assist system including a cannula apparatus as described herein.

Referring to FIG. 9, one embodiment of a cannula apparatus 310 is depicted as part of a ventricular assist system that includes a blood pump 350. The cannula apparatus 310 is attached and in fluid communication with an inlet end of the blood pump 350 through a fluid line 352 that includes a connector 354. The connector 354 is preferably configured to make a fluid-tight connection with the port of the cannula apparatus 310 (see, e.g., port 12 and threads 14 of cannula apparatus 10 of FIGS. 1-5).

The ventricular assist system of FIG. 9 also includes an outflow cannula 360 in fluid communication with the outlet of the blood pump 350. The outflow cannula may be designed for fluid connection to, e.g., an aorta (or other blood vessel) as is known in conventional VAD's (see, e.g., US 2004/0236170 (Kim)).

Figure 10:
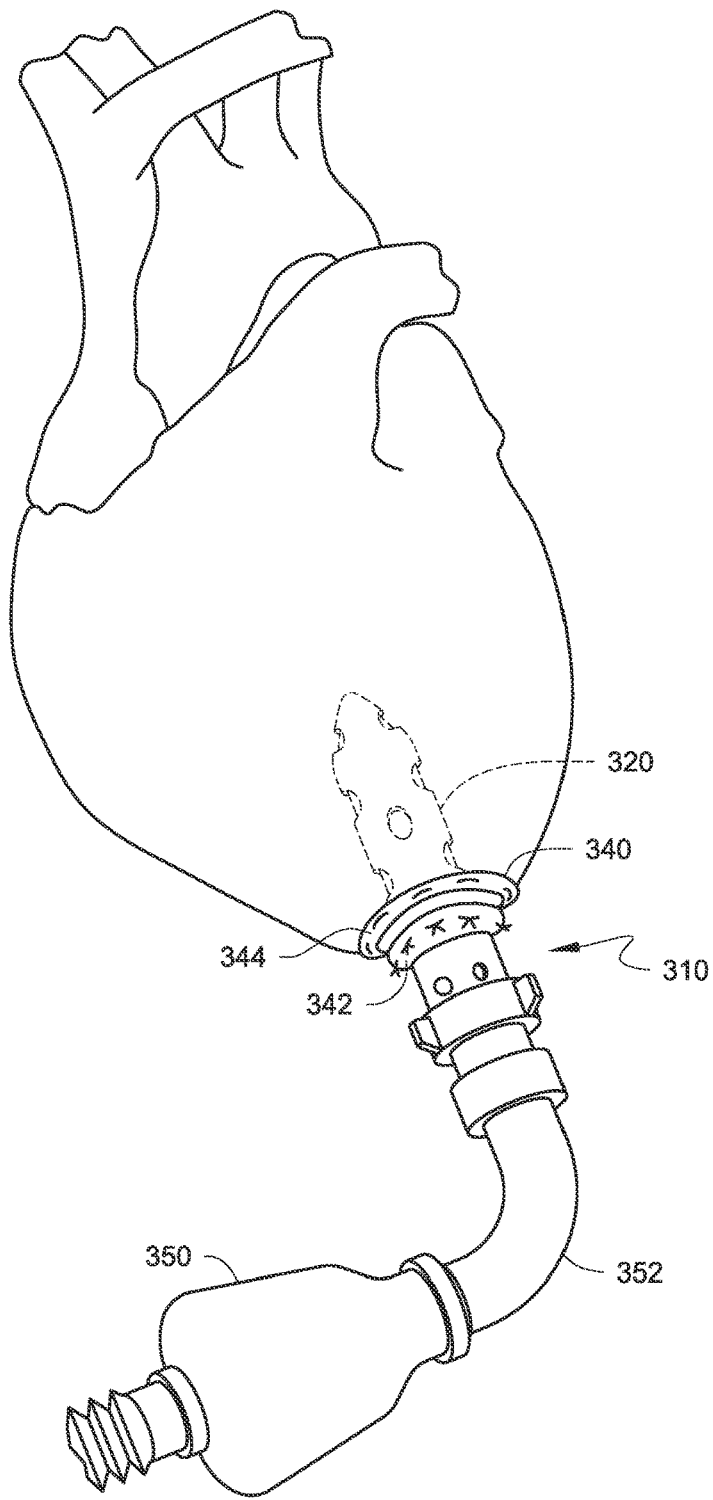
FIG. 10 is a perspective view of a portion of a ventricular assist system as described herein in which the inflow cannula apparatus is inserted into a ventricular chamber of a heart.

Referring to FIG. 10, a portion of the ventricular assist system of FIG. 9 is depicted with the cannula apparatus 310 positioned within the left ventricle of a heart. The attachment ring 340 is attached to the outer surface of the heart by sutures and the outer cannula 320 is seen within the left ventricle. In the depicted embodiment, the attachment ring 340 includes an inner layer 342 and an outer layer 344 of suture receptive material (e.g., felt). The inner ring 342 may be attached to the heart by, e.g., mattress sutures that extend from the outer ring 344 into the muscle and exit through the inner ring 342 to preferably promote eversion of myocardial muscle as seen between rings 342 and 344 in FIG. 10.

As discussed herein, the cannula apparatus 310 may preferably have a tapered distal end to assist in placement of the cannula apparatus within a ventricle. With a tapered distal end, the cannula apparatus 310 may be introduced trans-myocardially into the ventricle with the ventricular chamber full of blood and free of air. Interrupted pledgeted sutures can be placed around the apical myocardial dimple.

As described herein, one potential advantage of the cannula apparatus and the ventricular assist systems that use the cannula apparatus is the ability of the cannula apparatus to be primed before placement in the heart and to retain that priming during the placement process. One illustrative method of priming a ventricular assist system that includes a blood pump 350 and a cannula apparatus 310 attached to the inlet of the blood pump 350 (as depicted in, e.g., FIGS. 9 and 10) may include submerging the blood pump 350 and the cannula apparatus 310 in a selected blood-compatible liquid such as, e.g., saline, albumin, blood or other blood-based liquids, etc. The cannula apparatus 310 is preferably in the open arrangement either before or after the blood pump 350 and the cannula apparatus 310 are submerged. Furthermore, the cannula apparatus 310 may or may not be attached to the blood pump 350 before both components are submerged, i.e., the cannula apparatus 310 may be attached to the blood pump 350 after it has been submerged.

With the cannula apparatus 310 and the blood pump 350 both submerged and attached to each other with a fluid-tight connection, and with the cannula apparatus 310 in the open arrangement, the blood pump 350 is preferably operated to pull the selected liquid into the cannula apparatus 310 and the blood pump 350. After operation of the blood pump 350 to pull the selected liquid into the cannula apparatus 310 and the blood pump 350, the cannula apparatus 310 is moved to the closed arrangement while at least the cannula apparatus 310 remains submerged in the selected liquid (it may also be preferred that the blood pump 350 also remain submerged until the cannula apparatus 310 is moved to the closed arrangement). In the primed state, the cannula apparatus 310 and the blood pump 350 preferably contain the selected liquid in which they were submerged.

In some embodiments, the cannula apparatus 310 may include a relatively small opening into the interior volume of the cannula apparatus 310 proximate the distal tip 318 (see, e.g., FIG. 9) to ensure that the entire volume of the cannula apparatus 310 is filled with the selected liquid during the priming process. In some methods, a needle, catheter, or other fluid lumen may be inserted into the interior volume of the cannula apparatus 310 deliver selected liquid and/or exhaust any air that may be retained within the cannula apparatus during the priming process.

In some embodiments of the methods of priming as described herein, an outflow cannula 360 may be attached to an outlet of the blood pump 350 either while the blood pump 350 is submerged as a part of the priming process or after the primed blood pump 350 and cannula apparatus 310 have been removed from the selected liquid.

One exemplary method of placing a ventricular assist system as described herein in a left ventricle may include the following actions (although it should be understood that the cannula apparatus and the ventricular assist systems described herein may be placed by many different methods other than those described herein). A sternotomy (opening of chest) may be perforated on the patient receiving the system. The ventricular assist system may be primed and assembled as described herein. A side biting clamp may be used on the ascending aorta and outflow graft sewn to aorta off bypass. Interrupted pledgeted sutures can be placed around the apical myocardial dimple for later attachment to the sewing ring of the cannula apparatus. If needed to power the blood pump, an electrical driveline can be subcutaneously tunneled from an internal location to a location outside the body cavity.

With the patient preferably in the Trendeleburg position (head down), an epi-aortic probe can be used to find and define placement of the apical dimple. After the apical dimple is found, a stab wound can be placed within the center of the apical dimple and the tapered distal end of the primed cannula apparatus (which is in the closed arrangement) can then introduced trans-myocardially into the ventricle while the ventricular chamber is full of blood and free of air. After insertion into the ventricle, the cannula apparatus can then be moved from the closed arrangement to the open arrangement to allow blood within the ventricle to enter the cannula apparatus and advance towards the blood pump. The interrupted sutures can also be placed through an attachment ring on the cannula apparatus (and/or a standard suture whip stitch can be used to secure the attachment ring to the epicardial surface). If needed for operation, the electrical drive can be connected to the outer power source to activate the blood pump so that the ventricular assist system is ready for operative use.

Another feature that may be included in one or more embodiments of the cannula apparatus described herein is a guidewire lumen that may be used with a guidewire to facilitate deployment of the cannula apparatus within, e.g., a primary blood vessel, to augment cardiac output (such as, e.g., devices placed within femoral vessels). This feature may be incorporated into any of the cannula apparatus described herein. One potential benefit of a cannula apparatus as described herein that includes a guidewire lumen is placement without the need for a sternotomy to access the heart directly for VAD insertion. For example, the cannula apparatus may be deployed using percutanous insertion or via a direct surgical arteriovenous cutdown. Typically, in this manner, the femoral artery and vein are surgically isolated and a purse string suture is placed on the vessel surface. A large bore needle is introduced within the purse string and a guidewire is placed using, e.g., the Seldinger method. A vessel dilator could be then inserted over the guidewire to assist in the formation of an adequate opening within the purse string such that the cannula apparatus can be introduced over the guidewire.

Figure 11:
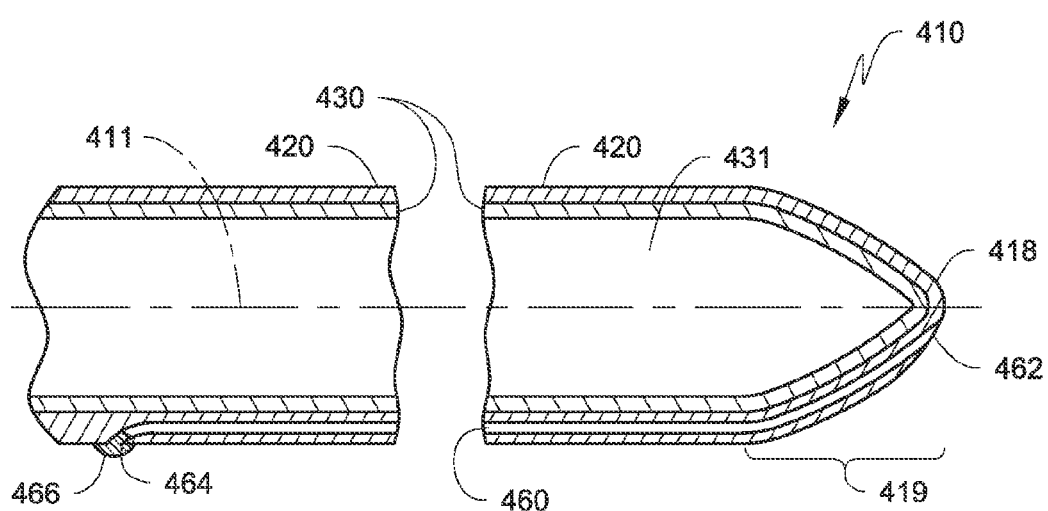
FIG. 11 is an enlarged cross-sectional view of a portion of another alternative embodiment of a cannula apparatus as described herein including a guidewire lumen.

One embodiment of a cannula apparatus 410 including a guidewire lumen is depicted in FIG. 11 in which the outer cannula 420 may include a guidewire lumen 460 that extends to a distal opening 462 proximate the distal tip 418 of the cannula apparatus 410. The guidewire lumen 460 is, in one or more embodiments, isolated from the remainder of the cannula apparatus 410 such that it provides no fluid access to the interior volume 431 defined within the inner cannula 430 of the cannula apparatus 410. The guidewire lumen 460 preferably terminates proximally of the distal tip 418 of the cannula apparatus 410 at a proximal opening 464. The proximal opening 464 may, in one or more embodiments that include an attachment ring or other attachment structure (see, e.g., attachment ring 40 in FIGS. 1 and 3), be located proximally of the attachment ring or other attachment structure such that a guidewire located in the guidewire lumen 460 can be removed after attachment of the cannula apparatus 410 using the attachment ring or other attachment structure. The proximal and distal direction of the features described herein are with reference to the longitudinal axis 411 depicted in FIG. 11. Although no openings are depicted in the outer cannula 420 and the inner cannula 430, it should be understood that such openings would be provided in the cannula apparatus 410 as described herein with respect to the other illustrative embodiments.

The proximal opening 464 of the guidewire lumen 460 may, in one or more embodiments, be closed after placement of the cannula apparatus and removal of any guidewire from the guidewire lumen 460. Closure of the guidewire lumen 460 may be accomplished by any suitable technique and/or structure. One example of a potential closure mechanism is the use of a plug 466 located in the proximal opening 464 of the guidewire lumen 460. The plug 466 may be held in place by any suitable technique, e.g., threads, friction, adhesives, etc.

Because the distal opening 462 of the guidewire lumen 460 is located within a volume occupied by blood (e.g., in the heart, a vessel, etc.) blood can flow into the guidewire lumen 460 through the distal opening 462 and exit through the proximal opening 464. Such flow can be useful to indicate proper placement of the cannula apparatus 410. The proximal opening 464 of the guidewire lumen 460 may then be closed as described herein.

Another optional feature of one or more embodiments of the cannula apparatus described herein that is also depicted in FIG. 11 is that the tapered portion 419 of the cannula apparatus maybe free from any openings that would allow flow into the interior volume 431. This feature may be incorporated into any of the cannula apparatus described herein. Although the depicted embodiment includes distal opening 462 of the guidewire lumen 460, that opening 462 and the remainder of the guidewire lumen 460 are isolated from the interior volume 431 as described herein. In the absence of any openings in the tapered portion 419, insertion of the cannula apparatus 410 may be facilitated.

The various devices, apparatus and components described herein may be constructed of any suitable material and/or combinations of materials known to those skilled in the art.

The complete disclosure of the patents, patent documents, and publications cited herein are incorporated by reference in their entirety as if each were individually incorporated.

Illustrative embodiments are discussed herein and reference has been made to some, but not all, possible variations within the scope of this invention. These and other variations and modifications will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A ventricular assist system comprising:
   a blood pump;
   an outflow cannula in fluid communication with an outlet of the blood pump;
   an inflow cannula apparatus comprising a port in fluid communication with an inlet of the blood pump, wherein the inflow cannula apparatus comprises:
   an outer cannula comprising a proximal end and a distal end, wherein the outer cannula further comprises:
      a sidewall defining an interior volume extending from the distal end of the outer cannula to the proximal end, wherein the distal end of the outer cannula is a closed distal end such that fluid cannot enter the outer cannula through the distal end of the outer cannula,
      a plurality of first openings extending through the sidewall into the interior volume of the outer cannula between the proximal end and the distal end of the outer cannula, wherein all of the first openings of the plurality of first openings are located proximally from the closed distal end of the outer cannula;
   an inner cannula comprising a proximal end and distal end, wherein at least a portion of the inner cannula is located within the interior volume of the outer cannula, and wherein the inner cannula further comprises:
      a sidewall defining an interior volume extending from the distal end of the inner cannula to the proximal end,
      a plurality of second openings extending through the sidewall into the interior volume of the inner cannula between the proximal end and the distal end of the inner cannula; and
   an attachment ring extending radially outward from a longitudinal axis extending through the cannula apparatus from the distal end of the outer cannula through the port;
   wherein the inner cannula and the outer cannula comprise an open arrangement in which the first openings and the second openings are aligned such that fluid from outside of the outer cannula can flow into the interior volume of the inner cannula through the first and second openings;
   wherein the inner cannula and the outer cannula comprise a closed arrangement in which the first openings and the second openings are offset such that the sidewall of the outer cannula blocks the plurality of second openings in the inner cannula and the sidewall of the inner cannula blocks the plurality of first openings in the outer cannula, wherein fluid from outside of the outer cannula does not flow into the interior volume of the inner cannula through the first and second openings;
   and wherein fluid flowing into the interior volume of the inner cannula through the second openings passes out of the cannula apparatus through the port.

2. A ventricular assist system according to claim 1, wherein the inner cannula and the outer cannula are configured to move relative to each other to selectively place the inner cannula and the outer cannula in the open arrangement or the closed arrangement.

3. A ventricular assist system according to claim 1, wherein the inner cannula and the outer cannula are configured to rotate relative to each other to selectively place the inner cannula and the outer cannula in the open arrangement or the closed arrangement.

4. A ventricular assist system according to claim 1, wherein the inner cannula and the outer cannula are configured for translational movement relative to each other to selectively place the inner cannula and the outer cannula in the open arrangement or the closed arrangement.

5. A ventricular assist system according to claim 1, wherein all of the first openings of the plurality of first openings in the outer cannula are aligned with the second openings of the inner cannula when the inner and outer cannulas are in the open arrangement.

6. A ventricular assist system according to claim 1, wherein only some of the first openings of the plurality of first openings in the outer cannula are aligned with the second openings of the inner cannula when the inner and outer cannulas are in the open arrangement.

7. A ventricular assist system according to claim 1, wherein a distal end of the cannula apparatus comprises a tapered distal end that narrows when moving distally along the cannula apparatus.

8. A ventricular assist system according to claim 1, wherein the cannula apparatus comprises a locking mechanism configured to lock the inner cannula and the outer cannula in the open arrangement and the closed arrangement, whereby movement out of the open arrangement or the closed arrangement is prevented when the inner and outer cannula are locked.

9. A ventricular assist system according to claim 8, wherein the locking mechanism comprises a locking pin.

10. A ventricular assist system according to claim 1, wherein the cannula apparatus further comprises a sealing element located between the inner cannula and the outer cannula at a location distal from the port of the cannula apparatus.

11. A ventricular assist system according to claim 10, wherein the sealing element is located proximal to all of the first openings and the second openings.

12. A ventricular assist system according to claim 1, wherein the port of the cannula apparatus comprises a connector configured for fluid-tight connection to a fluid line extending away from the port.

13. A ventricular assist system according to claim 1, wherein the cannula apparatus comprises a guidewire lumen isolated from the interior volume of the inner cannula.

* * * * *